US007838518B2

(12) United States Patent
Spinks et al.

(10) Patent No.: US 7,838,518 B2
(45) Date of Patent: Nov. 23, 2010

(54) 1-ARYLSULFONYL-3-SUBSTITUTED INDOLE AND INDOLINE DERIVATIVES USEFUL IN THE TREATMENT OF CENTRAL NERVOUS SYSTEM DISORDERS

(75) Inventors: Daniel Spinks, Newhouse-Scotland (GB); Richard E. Armer, Newhouse-Scotland (GB); David J. Miller, Newhouse-Scotland (GB); Zoran Rankovic, Newhouse-Scotland (GB); Gayle Spinks, Newhouse-Scotland (GB); Jordi Mestres, Newhouse-Scotland (GB); David Robert Jaap, Oss (NL)

(73) Assignee: N.V. Organon, Oss (NL)

( * ) Notice: Subject to any disclaimer, the term of this patent is extended or adjusted under 35 U.S.C. 154(b) by 826 days.

(21) Appl. No.: 10/504,556

(22) PCT Filed: Feb. 5, 2003

(86) PCT No.: PCT/EP03/50010

§ 371 (c)(1),
(2), (4) Date: Aug. 12, 2004

(87) PCT Pub. No.: WO03/068220

PCT Pub. Date: Aug. 21, 2003

(65) Prior Publication Data

US 2005/0154023 A1 Jul. 14, 2005

(30) Foreign Application Priority Data

Feb. 12, 2002 (EP) .................................. 02075584

(51) Int. Cl.
*A61K 31/55* (2006.01)
*C07D 403/02* (2006.01)

(52) U.S. Cl. .................. 514/218; 514/252.19; 514/402; 514/415; 540/575; 544/373; 546/306.1; 546/467

(58) Field of Classification Search ................ 514/218, 514/252.19, 402, 415; 540/575; 544/373; 548/306.1, 467

See application file for complete search history.

(56) References Cited

U.S. PATENT DOCUMENTS

| 4,803,199 A | 2/1989 | Donatsch et al. | |
| 6,187,805 B1* | 2/2001 | Pineiro et al. | 514/415 |
| 6,251,893 B1 | 6/2001 | Maddaford et al. | |
| 6,350,748 B1* | 2/2002 | Takeyama et al. | 514/235.2 |
| 6,613,781 B2* | 9/2003 | Zhou et al. | 514/323 |
| 6,767,912 B2* | 7/2004 | Zhou et al. | 514/300 |
| 6,916,812 B2* | 7/2005 | Poindexter et al. | 514/235.8 |
| 2006/0223890 A1* | 10/2006 | Ramakrishna et al. | 514/646 |

FOREIGN PATENT DOCUMENTS

| EP | 0 732 333 A1 | 9/1996 |
| WO | WO 96/03400 | 2/1996 |
| WO | WO 01/32660 A1 | 5/2001 |
| WO | WO02/41889 * | 5/2002 |

OTHER PUBLICATIONS

Pouihes et al. "First synthesis of marine . . . " CA 139:338117 (2003).*
Paxil Drug information Google search result (2007).*
Zhou et al. "4-(2-minoethoxy)-N- . . . " Bioorg. Med. Chem. Lett. v.15, p. 1393-1396 (2005).*
Silverman "The organic chemistry of drug design and drug action" p. viii-ix, 72 (1993).*
Kobayashi et al "Preparation of sulfonyl . . . " CA 132:194391 (2000).*
DiMalta et al. "Preparaion of N-phenylsulfonyl . . . " CA 138:137337 (2003).*
Spinks et al. "Preparation of 1-arylsulfonyl . . . " CA 139:197363 (2003).*
Ramakrishna et al. "Preparation of N-arylsulfonyl . . . " CA 141:38523 (2004).*
Bissantz et al. "Indole-3-carbonyl . . . " CA 146:163038 (2007).*
Rubini et al. "Synthesis of isosteric . . . " Tetrahedron v.42 p. 6039-45 (1986).*
Cole et al. "Discovery of N1-(6-chloroimidazo . . . " J. Med. Chem. v.50(23) p. 5535-5538 (2007).*
Cole et al. "Conformationally constrained . . . " Bioorg. med. chem. lett. v. 15 p. 4780-4785 (2005).*
Cole et al. "N-arylsuofonyl . . . " Bioorg. Med. Chem. Lett v. 15, p. 379-383 (2005).*
Derivative definition, biology on line, p. 1 (2009).*
Bourson A et al. "Determination of the role of . . . " J. Pharm. Exp. ther. v.274, p. 173-180 (1995).*
Ketch, Daniel; et. al., "A Convenient Synthesis of 3-Acylindoles via Friedel-Crafts Acylation of 1-(Phenylsulfonyl)indole. A New Route to Pyridocarbazole-5,11-quinones and Ellipticine", The Journal of Organic Chemistry; vol. 50, No. 26, 1985.
Russell, Michael, G.N; et. al., "N-Arylsulfonylindole Derivatives as Serotonin 5-HT$_6$ Receptor Ligands", J. Med. Chem, vol. 44, 2001, pp. 3881-3895.
Bourson et al., "Determination of the Role of the 5-ht$_6$ Receptor in the Rat Brain: A Study using Antisense Oligonucleotides," *J. Pharmacol. Exp. Ther.* 274 (1995) 173-180.
Caulfield et al., "The First Potent and Selective Inhibitors of the Glycine Transporter Type 2," *J. Med. Chem.* 44 (2001) 2679-2682.
Cheng et al., "Relationship Between the Inhibition Constant ($K_1$) And The Concentration Of Inhibitor Which Causes 50 Per Cent Inhibition ($I_{50}$) Of An Enzymatic Reaction," *Biochem. Pharmacol.* 22 (1973) 3099-3108.

(Continued)

*Primary Examiner*—Celia Chang
(74) *Attorney, Agent, or Firm*—Susan L. Hess

(57) ABSTRACT

The present invention relates to 1-arylsulfonyl-3 substituted indole or indoline derivatives having the general formula (I) (I) wherein the dotted line represents an optional bond; n is 0 or 1; m is 0-5 and Ar, R6-R11 are defined in the description. The invention further relates to pharmaceutical compositions comprising said derivatives, and to the use of these 1-arylsulfonyl-3-substituted indole or indoline derivatives in the treatment of central nervous disorders such as psychosis, schizophrenia, manic depressions, depressions, neurological disorders, cognitive enhancement, Parkinson's disease, amyotrophic lateral sclerosis, Alzheimer's disease and Huntington's disease.

6 Claims, No Drawings

OTHER PUBLICATIONS

Ketcha et al., "A Convenient Synthesis of 3-Acylindoles via Friedel-Crafts Acylation of 1-(Phenylsulfonyl)indole. A New Route to Pyridocarbazole-5,11-quinones and Ellipticine," *J. Org. Chem.* 50 (1985) 5451-5457.

Kohen et al., "Cloning, Characterization, and Chromosomal Localization of a Human 5-HT$_6$ Serotonin Receptor," *J. Neurochem.* 66 (1996) 47-56.

Monsma et al., "Cloning and Expression of a Novel Serotonin Receptor with High Affinity for Tricyclic Psychotropic Drugs," *Mol. Pharm.* 43 (1993) 320-327.

Ruat et al., "A Novel Rat Serotonin (5-HT$_6$) Receptor: Molecular Cloning, Localization and Stimulation of cAMP Accumulation," *Biochem. Res. Comm.* 193 (1993) 268-276.

Roth et.al.,"Binding of Typical and Atypical Antipsychotic Agents to 5-Hydroxytryptamine-6 and 5-Hydroxytryptamine-7 Receptors," *J. Pharmacol. Exp. Ther.* 268 (1994) 1403-1410.

Russell et al., "N-Arylsulfonylindole Derivatives as Serotonin 5-HT$_6$ Receptor Ligands," *J. Med. Chem.* 44 (2001) 3881-3895.

Sleight et al., "5-HT$_6$ and 5-HT$_7$ Serotonin Receptors: Molecular Biology and Pharmacology," *Neurotransmissions* 11 (1995) 1-5.

* cited by examiner

1-ARYLSULFONYL-3-SUBSTITUTED INDOLE AND INDOLINE DERIVATIVES USEFUL IN THE TREATMENT OF CENTRAL NERVOUS SYSTEM DISORDERS

The invention relates to 1-arylsulfonyl-3-substituted indole and indoline derivatives, to pharmaceutical compositions comprising the same as well as to the use of these 1-arylsulfonyl-3-substituted indol and indoline derivatives in the treatment of central nervous disorders.

5-Hydroxytryptamine (5-HT, serotonin) is a vital chemical entity for normal human and animal functions. It is synthesised in the body from typtophan and is distributed throughout the blood, cell wall of the gastrointestinal tract and in the central nervous system (CNS). Dysfunction of the human serotonergic system has been hypothesised to be the root of numerous medical ailments. Conditions such as pain, emesis, sleep pattern disruption, depression, anxiety, cognitive dysfunction, schizophrenia and attention deficit hyperactivity disorder (ADHD) have all been linked with an imbalance of 5-HT. Thus the use of new chemical entities to modulate the serotonergic system and thus relieve disease states is an important branch of chemotherapy.

Fourteen serotonin receptor sub-types are known which have been split into seven groups (5-$HT_{1-7}$). These are mostly 7-transmembrane G-protein coupled receptors with the exception of 5-$HT_3$ that is an ion channel. The 5-$HT_6$ receptor was first discovered in the rat in 1993 (Monsma F J, *Mol. Pharm.* 1993, 43, 320-327 and Raut M, *Biochem. Res. Comm.*, 1993, 193, 269-276) and in the human in 1996 (Kohen R, *J. Neurochem.*, 1996, 66, 47-56). The 5-$HT_6$ mRNA has been demonstrated to be localised in the rat brain and in particular in the olfactory tubercle, striatum, nucleus accumbens, dentate gyrus and CA1-3 fields of the hippocampus. The distribution in human tissue has been shown to mirror that of the rat.

Numerous antipsychotic and antidepressant drugs have affinity for the 5-$HT_6$ receptor. Clozapine, clorotepine, zotepine, and olanzapine are all very potent 5-$HT_6$ antagonists (Roth B L, *J. Pharmacol. Exp. Ther.*, 1993, 286, 1403-1410) whilst the tricyclic anti-depressants amoxipine, clomimprimine and amitriptyline also interact strongly (Monsma F J, *Mol. Pharm.* 1993, 43, 320-327).

Various ligands for the 5-$HT_6$ receptor have been identified and used to study the functional role of the receptor. Compounds having affinity for the 5-$HT_6$ receptor have been shown to be useful in the treatment of central nervous disorders such as psychosis, schizophrenia, manic depressions (Roth, B. I. et al. J. Pharmacol. Exp. Ther. 268, 1403-1410, 1994) depressions (Sibley, D. R. et al. Mol. Pharmacol. 43, 320-327, 1993), neurological disorders (Bourson, A. et al. J. Pharmacol. Exp. Ther. 274, 173-180, 1995), Parkinson's disease, amyotrophic lateral sclerosis, Alzheimer's disease and Huntington's disease (Sleight, A. J. et al., Neurotransmissions, 11, 1-5, 1995). 1-Arylsulfonyl-indol derivatives, which are substituted at the 3-position with a bicyclic piperidine or piperazine containing ring structure, are disclosed in U.S. Pat. No. 6,251,893 B1 (NPS Allelix Corp.) as compounds having affinity for the serotonin 5-$HT_6$ receptor and being useful in the treatment of CNS disorders mentioned above.

Structurally related $N_1$-arylsulfonyltryptamines, i.e. 1-arylsulfonyl-indol and indoline derivatives having an aminoethyl side chain at the 3-position, the amino group of which is either alkylated or part of a heterocycloalkyl group, were recently disclosed in U.S. Pat. No. 6,187,805 B1 (Merck Sharp Dohme Ltd.) as selective 5-$HT_6$ binding ligands (see also Russell, M. G. N. et al., J. Med. Chem. 2001, 44, 3881-3895).

There remains a need for further compounds which exert pharmacological effects through selective binding at the 5-$HT_6$ receptor as compared to the other serotonin receptors.

To this aim the present invention provides 1-arylsulfonyl-3-substituted indole and indoline derivatives having the general formula I

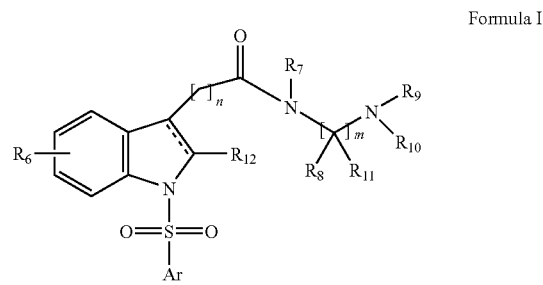

Formula I wherein Ar is a (hetero)aromatic group, optionally substituted with 1-5-substitutents selected from halogen, cyano, ($C_{1-4}$)alkyl (optionally substituted with halogen), ($C_{2-4}$)-alkenyl, ($C_{1-4}$)alkyloxy (optionally substituted with halogen), ($C_{6-12}$)aryl (optionally substituted with halogen or ($C_{1-4}$) alkyloxy), ($C_{6-12}$)aryloxy (optionally substituted with halogen), ($C_{6-12}$)arylsulfonyl, Het, di($C_{1-4}$)alkylamino, di($C_{1-4}$) alkylaminocarbonyl, ($C_{1-4}$)-alkanoyl or ($C_{1-4}$) alkanoylamino;

the dotted line represents an optional bond;

n is 0 or 1;

m is 0-5;

$R_6$ represents 1-4 substituents independently selected from H, ($C_{1-4}$)alkyl (optionally substituted with halogen), ($C_{1-4}$)alkyloxy (optionally substituted with halogen), ($C_{1-4}$)alkyl-oxycarbonyl, cyano, nitro and halogen;

$R_7$ is H, ($C_{1-4}$)alkyl, ($C_{6-12}$)aryl or ($C_{6-12}$)aryl($C_{1-4}$)alkyl; or $R_7$ together with $R_9$ or with one of $R_8$ complete a 4-, 5-, 6- or 7-membered saturated ring;

each $R_8$ is independently H, ($C_{1-4}$)alkyl or ($C_{6-12}$)aryl (optionally substituted with halogen, ($C_{1-4}$)alkyl or ($C_{1-4}$)alkyloxy); or one of $R_8$ together with $R_7$ or $R_9$ or the geminal $R_{11}$ complete a 4-, 5-, 6- or 7-membered saturated ring; and each other $R_8$ is independently H, ($C_{1-4}$)alkyl or ($C_{6-12}$)aryl (optionally substituted with halogen, ($C_{1-4}$)alkyl or ($C_{1-4}$)alkyloxy);

$R_9$ and $R_{10}$ are independently H, ($C_{1-4}$)alkyl, ($C_{6-12}$)aryl or ($C_{6-12}$)aryl($C_{1-4}$)alkyl; or $R_9$ and $R_{10}$ form together with the N to Which they are bonded a 5-, 6- or 7-membered saturated or unsaturated ring system, optionally containing an O-atom or a further N-atom, which may be substituted with ($C_{1-4}$)alkyl or ($C_{6-12}$)aryl($C_{1-4}$)alkyl; or $R_9$ together with $R_7$ or with one of $R_8$ complete a 5-, 6- or 7-membered saturated or unsaturated ring; and $R_{10}$ is H, ($C_{1-4}$)alkyl, ($C_{6-12}$)aryl or ($C_{6-12}$)aryl($C_{1-4}$)alkyl; or $R_{10}$ and one of $R_{11}$ complete a 4-, 5-, 6- or 7-membered saturated ring;

each $R_{11}$ is independently H or $(C_{1-4})$alkyl; or one of $R_{11}$ together with $R_{10}$ or with the geminal $R_8$ form a 4-, 5-, 6- or 7-membered saturated ring; and each other $R_{11}$ is independently H or $(C_{1-4})$alkyl;

or a pharmaceutically acceptable salt thereof, as ligands which selectively bind to the 5-HT$_6$ receptor and can therefore be used in the treatment of central nervous disorders such as psychosis, schizophrenia, manic depressions, depressions, neurological disorders, cognitive enhancement, Parkinson's disease, amyotrophic lateral sclerosis, Alzheimer's disease and Huntington's disease.

The 1-arylsulfonyl-3-substituted indole and indoline derivatives of the invention have either a N-substituted carbamoyl (aminocarbonyl; n is 0)) or a N-substituted carbamoylmethyl (n is 1) group as a characteristic 3-substituent. Preferred are the N-substituted N-carbamoyl derivatives (n is 0) according to formula I.

The indole derivatives of the invention are the compound of Formula I wherein the dotted line represents a bond. Compounds wherein this bond is absent are the indoline derivatives, i.e. the 2,3-dihydro-indole derivatives. The indoline derivatives of formula I are the preferred compounds of the invention.

The term (hetero)aryl as used in the definition of formula I, and indicated by Ar, means either an aryl or a heteroaryl group. Aryl represents a carbocyclic group containing 6-15 carbon atoms and consisting of 1, 2 or 3 (fused) rings, at least one of which is an aromatic ring. Examples of such aryl groups are phenyl, naphthyl, phenanthryl, indenyl and indanyl. Heteroaryl represents a cyclic system containing 2-14 carbon atoms and 1-3 heteroatoms selected from O, S and N, the system consisting of 1, 2 or 3 (fused) rings, at least one of which is aromatic. Examples of heteroaryl groups are thienyl, furyl, oxazolyl, oxadiazolyl, isoxazolyl, thiazolyl, isothiazolyl, furazanyl, benzofurazanyl, benzothienyl, benzoxazolyl, benzothiadiazolyl, 2,3-dihydrobenzofuranyl, 2,3-dihydrobenzodioxinyl, quinolinyl, isoquinolinyl, phenanthridinyl, chromanyl and isochromanyl.

The term $(C_{1-4})$alkyl, as used in the definition of formula I, means a branched or unbranched alkyl group having 1-4 carbon atoms, like butyl, isobutyl, tertiary butyl, propyl, isopropyl, ethyl and methyl.

In the term $(C_{1-4})$alkyloxy, $(C_{1-4})$alkyl has the meaning as defined above. Preferred $(C_{1-4})$alkyloxy groups are ethyloxy end methyloxy.

The term $(C_{2-4})$alkenyl means an alkenyl group having 2-4 carbon atoms, such as ethenyl (vinyl), 1-propenyl, isopropenyl, 2-propenyl or one of the isomers of butenyl.

The term halogen means F, Cl, Br, or I. When halogen is a substituent at an alkyl group, F is preferred. A preferred halogen substituted alkyl group is trifluoromethyl.

The term $(C_{6-12})$aryl means an aromatic group having 6-12 carbon atoms like for example phenyl, naphthyl, indenyl or indanyl. These aromatic groups may be substituted with halogen, $(C_{1-4})$alkyl or $(C_{1-4})$alkyloxy, wherein $(C_{1-4})$alkyl has the previously given meaning and may be substituted with halogen.

In the terms $(C_{6-12})$aryloxy and $(C_{6-12})$arylsulfonyl, as used in the definition of formula I, $(C_{6-12})$aryl has the meaning as defined above.

The term $(C_{6-12})$aryl$(C_{1-4})$alkyl, as used in the definition of Formula I, means a $(C_{1-4})$alkyl group which is substituted with a $(C_{6-12})$aryl group, both having the meaning as defined above. Examples are the benzyl group and the phenethyl (2-phenylethyl) group.

The term $(C_{1-4})$alkanoyl means $(C_{1-4})$alkylcarbonyl, wherein $(C_{1-4})$alkyl is as defined above, such as acetyl, propionyl, butyryl and isobutyryl.

The term Het means a 4-, 5- or 6-membered heterocycle containing one of more heteroatoms selected from O, S and N, such as pyridyl, thienyl, oxazolyl, oxadiazolyl, thiazolyl, and the like, and which may be substituted with $(C_{1-4})$alkyl, $(C_{1-4})$alkyloxy or halogen.

The N-atom of the carbamoyl group in the 3-position of the indol nucleus of the compounds of Formula I can be derived from a cyclic diamine, such as imidazolidine, piperazine, homopiperazine, when $R_9$ together with either $R_7$ complete a 4-, 5-, 6- or 7-membered saturated ring. The preferred cyclic diamine is the homopiperazine ring system.

In the definition of formula I one of $R_8$ may together with $R_7$ or $R_9$ or the geminal $R_{11}$ complete a 4-, 5-, 6- or 7-membered saturated ring. These saturated rings are the azetidine ring, the pyrrolidine ring, the piperidine and the azepine ring, respectively. The same saturated rings may also be formed when $R_{10}$ and $R_{11}$ are combined to complete a ring.

In the definition of formula I $R_9$ and $R_{10}$ may form together with the N to which they are bonded a 5-, 6- or 7-membered saturated or unsaturated ring system, optionally containing an oxygen or a further N-atom. Examples of such ring systems are pyrrolidine, piperidine, azepine, diazetidine, imidazole, pyrazole, piperazine and diazepine and morpholine. Preferred ring systems formed by $R_9$ and $R_{10}$ are the morpholine and the piperazine ring.

There is a preference for compounds of the invention wherein the (hetero)aromatic group Ar in formula I is selected from phenyl, naphthyl, thienyl, furyl, benzothienyl, benzothiadiazolyl, 2,3-dihydrobenzofuranyl, 2,3-dihydrobenzodioxinyl, quinolinyl, and isoquinolinyl. Especially preferred among these heteroaromatic groups are phenyl, 1-naphthyl, 2-naphthyl, 1-thienyl, 2-thienyl and benzothienyl.

Further preferred compounds of the invention correspond to formula I wherein m is 2, all of $R_8$ and $R_{11}$ are H, $R_{10}$ is H or $(C_{1-4})$alkyl and $R_7$ together with $R_8$ complete a [1,4]diazepan-1-yl group.

Also preferred are the 1-arylsulfonyl-3-substituted indole and indoline derivatives of the general formula I(a)

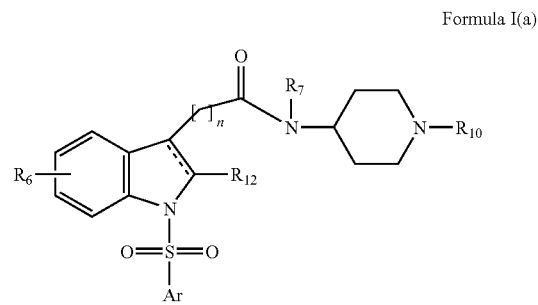

Formula I(a)

wherein the dotted line represents an optional bond and n, $R_6$, $R_7$, $R_{10}$, $R_{12}$ and Ar are as defined above for formula I.

One embodiment of the invention corresponds to 1-arylsulfonyl-3-substituted indole and indoline derivatives of the general formula I(b)

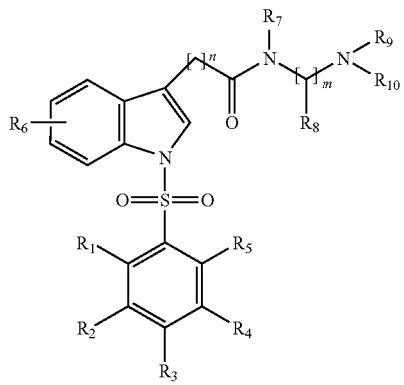

Formula I (b)

$R_1$ and $R_2$ are independently H, $(C_{1-4})$alkyl or $(C_{1-4})$alkyloxy; or $R_1$ and $R_2$ form together with the carbon atoms to which they are bonded a fused benzene ring;

$R_3$, $R_4$ and $R_5$ are independently H, $(C_{1-4})$alkyl or $(C_{1-4})$alkyloxy;

$R_6$ represents 1-4 substituents independently selected from H, $(C_{1-4})$alkyl (optionally substituted with halogen), $(C_{1-4})$alkyloxy (optionally substituted with halogen) and halogen;

$R_7$ is H or $(C_{1-4})$alkyl; or $R_7$ together with $R_9$ or with one of $R_8$ complete a 5-, 6- or 7-membered saturated ring;

each $R_8$ is independently H or $(C_{1-4})$alkyl; or one of $R_8$ together with $R_7$ or $R_9$ complete a 5-, 6- or 7-membered saturated ring;

and each other $R_8$ is independently H or $(C_{1-4})$alkyl;

$R_9$ and $R_{10}$ are independently H, $(C_{1-4})$alkyl or $(C_{6-12})$aryl$(C_{1-4})$alkyl; or l $R_9$ and $R_{10}$ form together with the N to which they are bonded a 5- or 6-membered saturated or unsaturated ring system, optionally containing a further N-atom, which may be substituted with $(C_{1-4})$alkyl or $(C_{6-12})$aryl$(C_{1-4})$alkyl; or $R_9$ together with $R_7$ or with one of $R_8$ complete a 5-, 6- or 7-membered saturated ring; and $R_{10}$ is H, $(C_{1-4})$alkyl or $(C_{6-12})$aryl$(C_{1-4})$alkyl;

or a pharmaceutically acceptable salt thereof,

Particularly preferred 1-arylsulfonyl-3-substituted indole and indoline derivatives according to the invention are:

1-(4-methoxynaphthalene-1-sulfonyl)-2,3-dihydro-1H-indole-3-carboxylic acid [2-(1-methyl-pyrrolidin-2-yl)-ethyl]amide (1);
1-(4-methoxynaphthalene-1-sulfonyl)-2,3-dihydro-1H-indole-3-carboxylic acid (1-methyl-piperidin-3-yl)amide (2);
1-(4-ethoxynaphthalene-1-sulfonyl)-2,3-dihydro-1H-indole-3-carboxylic acid homopiperazin-1-yl amide (8);
[1-(4-methoxynaphthalene-1-sulfonyl)-2,3-dihydro-1H-indol-3-yl]-piperazin-1-yl]-methanone (17);
(4-methoxynaphthalene-1-sulfonyl)-2,3-dihydro-1H-indole-3-carboxylic acid (2-diethylamino-ethyl)-amide (24);
1-(4-methoxynaphthalene-1-sulfonyl)-2,3-dihydro-1H-indole-3-carboxylic acid (1-methyl-piperidin-4-yl)-amide (25);
1-(4-methoxynaphthalene-1-sulfonyl)-2,3-dihydro-1H-indole-3-carboxylic acid (8-methyl-8-aza-bicyclo[3.2.1]oct-3-yl)amide (31);
[1,4]-diazepan-1-yl)-[1-(4-methoxynaphthalene-1-sulfonyl)-2,3-dihydro-1H-indol-3-yl]-methanone (34);
1-(4-methoxynaphthalene-1-sulfonyl)-2,3-dihydro-1H-indole-3-carboxylic acid methyl-(1-methyl-piperidin-4-yl)-amide (35);
1-(3-trifluoromethyl-benzenesulfonyl)-2,3-dihydro-1H-indole-3-carboxylic acid methyl-(1-methyl-piperidin-4-yl)-amide trifluoroacetate (39);
1-(3-bromo-benzenesulfonyl)-2,3-dihydro-1H-indole-3-carboxylic acid methyl-(1-methyl-piperidin-4-yl)-amide trifluoroacetate (40);
1-(4-trifluoromethoxy-benzenesulfonyl)-2,3-dihydro-1H-indole-3-carboxylic acid methyl-(1-methyl-piperidin-4-yl)-amide trifluoroacetate (42);
1-(5-bromo-thiophene-sulfonyl)-2,3-dihydro-1H-indole-3-carboxylic acid methyl-(1-methyl-piperidin-4-yl)-amide trifluoroacetate (43);
1-(4-bromo-5-chloro-thiophene-sulfonyl)-2,3-dihydro-1H-indole-3-carboxylic acid methyl-(1-methyl-piperidin 4-yl)-amide trifluoroacetate (44);
1-(4,5-dibromo-thiophene-sulfonyl)-2,3-dihydro-1H-indole-3-carboxylic acid methyl-(1-methyl-piperidin-4-yl)-amide trifluoroacetate (47);
1-(4-trifluoromethyl-benzenesulfonyl)-2,3-dihydro-1H-indole-3-carboxylic acid methyl-(1-methyl-piperidin-4-yl)-amide trifluoroacetate (50);
1-(2,5-dichloro-thiophene-3-sulfonyl)-2,3-dihydro-1H-indole-3-carboxylic acid methyl-(1-methyl-piperidin-4-yl)-amide trifluoroacetate (51);
1-(2,3-dihydro-benzofuran-5-sulfonyl)-2,3-dihydro-1H-indole-3-carboxylic acid methyl-(1-methyl-piperidin-4-yl)-amide trifluoroacetate (55);
1-(naphthalene-2-sulfonyl)-2,3-dihydro-1H-indole-3-carboxylic acid methyl-(1-methyl-piperidin-4-yl)-amide trifluoroacetate (58);
1-(naphthalene-1-sulfonyl)-2,3-dihydro-1H-indole-3-carboxylic acid methyl-(1-methyl-piperidin-4-yl)-amide trifluoroacetate (59);
1-(biphenyl-3-sulfonyl)-2,3-dihydro-1H-indole-3-carboxylic acid methyl-(1-methyl-piperidin-4-yl)-amide trifluoroacetate (60);
1-(benzo[b]thiophene-3-sulfonyl)-2,3-dihydro-1H-indole-3-carboxylic acid methyl-(1-methyl-piperidin-4-yl)-amide trifluoroacetate (62);
1-(3-bromo-4-methoxy-benzenesulfonyl)-2,3-dihydro-1H-indole-3-carboxylic acid methyl-(1-methyl-piperidin-4-yl)-amide trifluoroacetate (69);
1-(5-chloro-naphthalene-1-sulfonyl)-2,3-dihydro-1H-indole-3-carboxylic acid methyl-(1-methyl-piperidin-4-yl)-amide trifluoroacetate (71); and
1-(5-methyl-2-trifluoromethyl-furan-3-sulphonyl)-2,3-dihydro-1H-indole-3-carboxylic acid methyl-(1-methyl-piperidyn-4-yl)-amide (109).

The 1-arylsulfonyl-3-substituted indole and indoline derivatives of Formula I can be prepared from the condensation of a 1-arylsulfonyl-3-carboxylic acid indole or indoline derivative of Formula II, wherein $R_6$, $R_{12}$ and n have the meaning as previously defined,

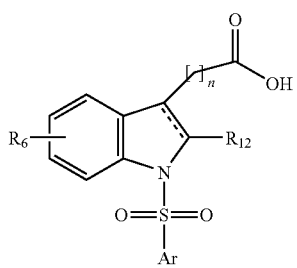

Formula II with a diamine derivative of Formula III, wherein $R_7$-$R_{11}$ and m have the meaning

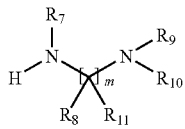

Formula III as previously defined. Such condensations can be carried out using for instance in situ activation of the carboxylic acid function of compounds of Formula II with activating agents such as diisopropylcarbodiimide, dicyclohexylcarbodiimide, benzotriazol-1-yl-oxy-tris-pyrrolidinophosphonium hexafluorophosphate (PyBOP®), 2-(1H-benzotriazole-1-yl)-1,1,3,3-tetramethyluronium tetrafluoroborate (TBTU) and the like.

The 1-arylsulfonyl-3-carboxylic acid indole or indoline derivatives formula II can be obtained from the acylation of an indole- or indoline-3-carboxylic acid ethyl ester (or an alternative alkylester) derivative of formula IV, wherein $R_6$, $R_{12}$ and n have the meaning as previously defined,

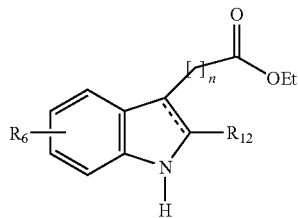

Formula IV with a phenylsulfonylhalide derivative according to Formula V, wherein Hal is Cl, Br or I, preferably Cl, and Ar has the meaning as previously defined.

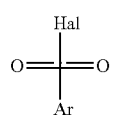

Formula V followed by saponification of the resulting ethyl ester derivative.

Compounds according to Formulas IV and V are either commercially available or can be prepared using chemical methods well known to the skilled person (see for instance: Ketcha, D. M. and Gribble, G. W., J. Org. Chem. 50, 5451-5457, 1985 and "Comprehensive Heterocyclic Chemistry", Alan R. Katitzky and Charles W. Rees, 1984, Pergamon Press Ltd.).

In a further aspect of the invention there is provided a pharmaceutical composition comprising a 1-arylsulfonyl-3-substituted indole or indoline derivative of formula I, or a pharmaceutically acceptable salt thereof, together with a pharmaceutically acceptable carrier thereof.

Compounds according to Formula I may contain one or more asymmetric carbon atoms and can than be obtained as a pure stereoisomer or as a mixture of stereoisomers. The present invention includes all possible stereoisomers within its scope, and each of the individual enantiomers and diastereomers and their salts, substantially free, i.e. associated with less than 5%, preferably less than 2%, in particular less than 1% of the other enantiomer, and mixtures of such stereoisomers in any proportions including the racemic mixtures containing substantially equal amounts of the two enantiomers. Methods for asymmetric synthesis whereby the pure stereoisomers are obtained are well known in the art, e.g. synthesis with chiral induction, enantioselective enzymatic ester hydrolysis, crystallization of salts which are obtained from optically active acids and the racemic mixture, separation of stereoisomers or enantiomers using chromatography on chiral media, or on straight phase or reversed phase chromatography media. Such methods are for example described in Chirality in Industry (edited by A. N. Collins, G. N. Sheldrake and J. Crosby, 1992; John Wiley).

The compounds of the invention may exist in unsolvated as well as in solvated forms with pharmaceutically acceptable solvents such as water, ethyl alcohol and the like. In general, the solvated forms are considered equivalent to the unsolvated forms for the purpose of the invention.

The ability of the compounds of the invention to interact with the 5-HT$_6$ receptor is established in (competitive) binding studies to NIH 3T3 cells stably expressing the human 5-HT$_6$ receptor.

Pharmaceutically acceptable salts of the compounds of Formula I may be obtained by treating the free base of the compounds according to Formula I with a mineral acid such as hydrochloric acid, phosphoric acid, sulfuric acid, preferably hydrochloric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid and the like.

The compounds of the present invention may be used in the treatment of mammals, including humans. The compounds are then used medically to care for, or deal with, an existing problem, e.g. a CNS disorder, such as such as psychosis, schizophrenia, manic depressions, depressions, neurological disorders, Parkinson's disease, amyotrophic lateral sclerosis, Alzheimer's disease and Huntington's disease. The compounds may also be used prophylactically to prevent the occurrence or reoccurrence of the mentioned disorders. The compounds of the invention may be administered for humans in a sufficient amount and for a sufficient amount of time to alleviate the symptoms associated with the disorders. Illustratively, daily dosage levels for humans can be in the range of 0.001-50 mg per kg body weight, preferably in a daily dosage of 0.01-20 mg per kg body weight.

The pharmaceutical compositions for use according to the invention comprise a 1-arylsulfonyl-3-substituted indole or indoline derivative having formula I or a pharmaceutically acceptable salt thereof in admixture with pharmaceutically acceptable auxiliaries, and optionally other therapeutic agents. The term "acceptable" means being compatible with the other ingredients of the composition and not deleterious to the recipients thereof. The compositions can be prepared in accordance with standard techniques such as those described in the standard reference, Gennaro, A. R. et al., Remington: *The Science and Practice of Pharmacy* (20th Edition, Lippincott Williams & Wilkins, 2000, see especially Part 5: Pharmaceutical Manufacturing). Compositions include e.g. those suitable for oral, sublingual, intranasal, subcutaneous, intravenous, intramuscular, local, or rectal administration, and the like, all in unit dosage forms for administration. For oral administration, the active ingredient may be presented as discrete units, such as tablets, capsules, powders, granulates, solutions, and suspensions.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

The invention further includes a pharmaceutical composition, as hereinbefore described, in combination with packaging material suitable for said composition, said packaging material including instructions for the use of the composition for the use as described previously within the description.

The invention is illustrated by the following examples.

GENERAL EXPERIMENTAL DETAILS

All mass spectrometry was carried out on either a PE SCIEX API 150EX or a PE SCIEX API 365 machine.

Example 1

1-(4-Methoxynaphthalene-1-sulfonyl)-2,3-dihydro-1H-indole-3-carboxylic acid [2-(1-methyl-pyrrolidin-2-yl)-ethyl]amide (1)

(A): 2,3-Dihydro-1H-indole-3-carboxylic acid

A stirred suspension of 1H-indole-3-carboxylic acid (20.8 g, 0.129 mol) in 1-butanol (600 cm$^3$) under nitrogen was heated under gentle reflux. Sodium (39.3 g, 1.71 mol) was added in small pieces over 3.5 h. After heating under reflux for a further 1.25 h the mixture was cooled and water (250 cm$^3$) was added carefully. The resulting mixture was concentrated almost to dryness and the residue was acidified by the careful addition of 2M hydrochloric acid (900 cm$^3$) with cooling. The aqueous mixture was washed with dichloromethane (2×300 cm$^3$) and then was neutralised by the addition of 5%, aqueous sodium bicarbonate solution (ca. 450 cm$^3$). The solution was evaporated to dryness under reduced pressure and the solid residue was triturated with dichloromethane-methanol (9:1, 400 cm$^3$ then 3×200 cm$^3$) to dissolve the product. The sodium chloride was filtered off and the filtrate was evaporated to afford a gum (18.1 g), which was dissolved in dichloromethane-methanol (9:1, 200 cm$^3$). This mixture was evaporated to low volume before diethyl ether was added, then the solvent was evaporated to leave a froth. This was triturated with diethyl ether (150 cm$^3$), filtered off and dried at 30° C. under vacuum to give the title compound (15.9 g, 76%): positive ion ESI (M+H)$^+$ 164.5.

(B): 4-methoxy-1-naphthyl sulfonyl chloride

To a cooled (0° C.) solution of 1-methoxy naphthalene (5 cm$^3$, 34.5 mmol) in dichloromethane (20 cm$^3$) was added, over a 10 minute period, chlorosulfonic acid (4.6 cm$^3$, 69.0 mmol). Following this addition, phosphorus pentachloride (7.2 g, 34.5 mmol) was added and the reaction was maintained at 0° C. for a further 45 min. The reaction was then quenched by pouring onto ice/water (50 cm$^3$), and allowed to warm to room temperature. Further dichloromethane (40 cm$^3$) was added and the solution was transferred to a separating funnel, where the organic layer was collected and washed with saturated aqueous sodium chloride solution (70 cm$^3$) and dried over sodium sulfate. The solvent was then evaporated under reduced pressure to afford title compound (8.23 g, 32.1 mmol; 93%).

(C): 1-(4-methoxynaphthalene-1-sulfonyl)-2,3-dihydro-1H-indole-3-carboxylic acid To 2,3-dihydro-1H-indole-3-carboxylic acid (A) (3.59 g, 22.0 mmol) was added aqueous N,N-dimethylformamide (DMF) (3:2 v/v; 75 cm$^3$), and then N,N-diisopropylethylamine (9.0 cm$^3$, 50.7 mmol). The mixture was stirred at room temperature for 5 min, before 4-methoxy-1-naphthyl sulfonyl chloride (B)(5.64 g, 22.0 mmol) was added. After stirring for a further 16 h at room temperature saturated aqueous sodium bicarbonate (60 cm$^3$) was added and the organic material was extracted into ethyl acetate (60 cm$^3$). The organic layer was then washed with a further portion of saturated aqueous sodium bicarbonate (40 cm$^3$) before the aqueous fractions were combined and acidified to pH 5 with 5N hydrochloric acid. The desired material was then extracted from the acidified aqueous mixture into ethyl acetate (2×60 cm$^3$), which was subsequently dried over sodium sulfate and evaporated under reduced pressure to afford the title compound (C) (6.1 g, 16.1 mmol, 73%).

(D): 1-(4-Methoxynaphthalene-1-sulfonyl)-2,3-dihydro-1H-indole-3-carboxylic acid [2-(1-methyl-pyrrolidin-2-yl)-ethyl]amide (1)

To a solution of 1-(4-methoxynaphthalene-1-sulfonyl)-2,3-dihydro-1H-indole-3-carboxylic acid (C) (900 mg, 2.35 mmol) in dichloromethane (20 cm$^3$) was added 1-hydroxybenzotriazole (HOBT, 0.48 g, 3.53 mmol) and 1,3-diisopropylcarbodidiimide (DIC, 0.55 cm$^3$, 3.53 mmol). This was left to stir at room temperature for 5 min, before adding 2-(1-methyl-pyrrolidin-2-yl)-ethylamine (0.342 cm$^3$, 2.35 mmol). The reaction was stirred for 16 h at room temperature before water (60 cm$^3$) was added followed by dichloromethane (60 cm$^3$). The resulting mixture was then shaken and the organic layer was washed with water (40 cm$^3$), saturated aqueous sodium bicarbonate solution (40 cm$^3$), water again (40 cm$^3$) and then saturated aqueous sodium chloride solution (50 cm$^3$) before the organic portion was dried over sodium sulfate, It was then evaporated under reduced pressure to afford the title compound (1) (800 mg, 1.62 mmol, 69%), positive ion ESI (M+H)$^+$ 494.6.

Example 2

1-(4-Methoxynaphthalene-1-sulfonyl)-2,3-dihydro-1H-indole-3-carboxylic acid (1-methyl-piperidin-3-yl)amide (2)

(A): Methanesulfonic acid 1-methylpiperidin-3-yl ester

To a solution of 3-hydroxy-N-methyl piperidine (2 cm$^3$, 17.4 mmol) in dichloromethane (40 cm$^3$) was added triethylamine (3.6 cm$^3$, 26.05 mmol) and then methanesulfonyl chloride (1.5 cm$^3$, 19:1 mmol). The reaction was then stirred for 3 h before a further aliquot (0.2 equiv., 3.47 mmol) of methanesulfonyl chloride was added. Stirring was continued for another 2 h at room temperature before the reaction was treated with water (60 cm$^3$) and extracted into dichloromethane (40 cm$^3$). The organic layer was washed with saturated aqueous sodium chloride solution (60 cm$^3$) and dried over sodium sulfate before being evaporated under reduced pressure to afford (A) (2.18 g, 11.28 mmol, 65%).

(B): 3-Azido-1-methylpiperidine

To a stirred solution of methanesulfonic acid 1-methylpiperidin-3-yl ester (A) (3 g, 0.17 mmol) in DMF (35 cm$^3$) was added sodium azide (11 g, 0.17 mol). The reaction was then heated to 80° C. for 16 h, and allowed to cool before water (80 cm$^3$) was added and the organic material was extracted into ethyl acetate (80 cm$^3$). The aqueous layer was then extracted with a further portion ethyl acetate (60 cm$^3$) and the combined organic collections and washed with saturated aqueous sodium chloride solution (100 cm$^3$). The organic mixture was and dried over sodium sulfate and then evaporated under reduced pressure to afford the title compound as a crude oil, which was used as crude in next reaction.

(C): 3-Amino-1-methylpiperidine

3-Azido-1-methylpiperidine (B, 5.3 mmol) was taken into methanol (20 cm$^3$) to which was added (10%) palladium on carbon (1 mmol). The flask was then fitted to hydrogenation apparatus and stirred at room temperature under 3 mbar of hydrogen for 3 h. The catalyst was then filtered off and the solvent removed under reduced pressure to afford the title compound (C) as an oil which was used as in next reaction without purification.

(D): 1-(4-Methoxynaphthalene-1-sulfonyl)-2,3-dihydro-1H-indole-3-carboxylic acid (1-methylpiperidin-3-yl)amide (2)

Prepared as in Example 1 (D). Positive ion ESI (M+H)$^+$ 480.6.

Example 3

1-(4-Methoxy-naphthalene-1-sulfonyl)-2,3-dihydro-1H-indole-3-carboxylic acid piperidin-3-ylamide (3)

(A): 3-{[1-(4-Methoxy-naphthalene-1-sulfonyl)-2,3-dihydro-1H-indole-3-carbonyl]-amino}-piperidine-1-carboxylic acid tert-butyl ester Prepared as in Example 1 (D).

(B): 1-(4-Methoxy-naphthalene-1-sulfonyl)-2,3-dihydro-1H-indole-3-carboxylic acid piperidin-3-ylamide (3)

To a solution of (A) (500 mg, 0.99 mmol) in dichloromethane (12 cm$^3$) was added, with stirring, trifluoroacetic acid (2 cm$^3$). The reaction was then allowed to stir at room temperature for 3 h, after which the solvents were removed by evaporation under reduced pressure. Dichloromethane (40 cm$^3$) was added to the residue and the mixture was then washed with saturated aqueous sodium bicarbonate solution (30 cm$^3$) followed by water (30 cm$^3$) and saturated sodium chloride solution (50 cm$^3$). The resulting organic mixture was then dried over sodium sulfate and evaporated under reduced pressure to afford the title compound as a pale yellow solid (310 mg, 0.77 mmol; 77%). Positive ion ESI (M+H)$^+$ 466.6.

Example 4

1-(4-Methoxy-2,3-dimethylbenzenesulfonyl)-2,3-dihydro-1H-indole-3-carboxylic acid (1-methyl-pyrrolidin-2-ylmethyl)amide (4)

(A): 2,3-dimethyl-4-methoxy benzene-1-sulfonyl chloride 2,3-Dimethylanisole (1 cm$^3$, 7.23 mmol) was dissolved into dichloromethane (4 cm$^3$) and cooled to 0° C. Chlorosulfonyl chloride (2 cm$^3$, 30.0 mmol) was then added dropwise, over 10 min and once the addition was completed the mixture was allowed to warm to room temperature and stirred for a further 45 min. The reaction was then quenched by the slow addition of ice/water (50 cm$^3$, CARE, exotherm) before further dichloromethane (30 cm$^3$) and water (30 cm$^3$) were added and the organic layer was collected. The aqueous layer was washed with dichloromethane (15 cm$^3$) and then organic extracts were combined and washed with saturated aqueous sodium chloride solution (70 cm$^3$) before being dried over sodium sulfate. The solvent was evaporated under reduced pressure to afford title compound (1.6 g, 6.82 mmol, 94% yield).

(B): 1-(2,3-dimethyl-4-methoxy benzene-1-sulfonyl)-2,3-dihydro-1H-indole-3-carboxylic acid: prepared as in Example 1 (C)

(C): 1-(4-Methoxy-2,3-dimethyl-benzenesulfonyl)-2,3-dihydro-1H-indole-3-carboxylic acid (1-methyl-pyrrolidin-2-ylmethyl)-amide (4)

Prepared as in Example 1 (D). Positive ion ESI (M+H)$^+$ 472.6.

Example 5

5-Methoxy-1-(4-methoxy-2,3,6-trimethyl-benzenesulfonyl)-2,3-dihydro-1H-indole-3-carboxylic acid methyl-(1-methyl-piperidin-4-yl)-amide (5)

(A): 5-Methoxyindole-3-carboxylic acid ethyl ester

To a solution of 5-methoxyindole (10.0 g, 67.9 mmol) in anhydrous diethyl ether (200 cm$^3$) being maintained at 0° C. under a nitrogen atmosphere was added a solution of ethyl magnesium bromide in diethyl ether (3.0 M, 22.65 cm$^3$, 67.95 mmol) over a period of ca. 10 min. The reaction was heat to reflux for 45 min, cooled to −5° C. and ethyl chloroformate (6.5 cm³, 67.9 mmol) was added. After stirring at this temperature for 1 h, the mixture was heated to reflux for 30 min, cooled and added to ice containing sat. aqueous ammonium chloride solution (150 cm³). This mixture was extracted into ethyl acetate (150 cm³), washed with water (3×150 cm³), dried (MgSO$_4$) and evaporated under reduced pressure to afford a brown oil (13.21 g), crystallisation from diethyl-ether/heptane afforded the title compound (4.95 g, 33%). Positive ion ESI (M+H)$^+$ 220.0.

(B): 5-Methoxyindole-3-carboxylic acid

To a solution of (R)-5-methoxyindole-3-carboxylic acid ethyl ester (6.19 g, 28.1 mmol) in ethyl alcohol (400 cm³) was added aqueous sodium hydroxide solution (4N, 42.0 cm³). Following addition the mixture was heated to reflux for 19.5 h. Upon cooling, the ethyl alcohol was removed under reduced pressure before water (150 cm³) was added and the mixture was Washed with dichloromethane (50 cm³) to remove any non-acidic material (1.48 g). The aqueous layer was acidified with hydrochloric acid (5N, 80 cm³) to precipitate an off-white solid which was filtered, washed with water (3×100 cm³), and dried in vacuo to afford the title compound (3.78 g, 70%). Positive ion ESI (M+H)$^+$ 192.1.

(C): 5-Methoxy-2,3-dihydro-1H-indole-3-carboxylic acid

Prepared as for 2,3-dihydro-1H-indole-3-carboxylic acid as exemplified in Helv. Chem. Acta 55 (1972) 2919-2933. Positive ion ESI (M+H)$^+$ 194.

(D): 5-Methoxy-1-(4-methoxy-2,3,6-trimethyl-benzenesulfonyl)-2,3-dihydro-1H-indole-3-carboxylic acid: Prepared as in Example 1 (C)

(E): 5-Methoxy-1-(4-methoxy-2,3,6-trimethyl-benzenesulfonyl)-2,3-dihydro-1H-indole-3-carboxylic acid methyl-(1-methyl-piperidin-4-yl)-amide (5)

Prepared as in Example 1 (D). Positive ion ESI (M+H)$^+$ 516.1.

Example 6

[1-(4-Methoxy-naphthalene-1-sulfonyl)-1H-indole-3-yl]-piperazin-1-yl-methanone (6)

(A): 1-(4-Methoxy-naphthalene-1-sulfonyl)-1H-indole-3-carboxylic acid

To a solution of 1H-indole-3-carboxylic acid (0.5 g, 3.1 mmol) in tetrahydrofuran (20 cm³ at 0° C. was added sodium bis(trimethylsilyl)amide (6.2 cm³, 6.2 mmol) dropwise under nitrogen. The solution was stirred at 0° C. for 30 m before addition of 4-methoxy-1-naphthyl sulfonyl chloride (0.8 g, 3.1 mmol) and the resultant solution was stirred at room temperature for 18 h. The solution was diluted with saturated aqueous sodium bicarbonate solution and washed with ethyl acetate. The aqueous layer was acidified to pH 1 with 5N hydrochloric acid and the product extracted into ethyl acetate. The organic layer was dried over magnesium sulfate, filtered and the filtrate evaporated under reduced pressure to give the title compound (A) (1.1 g, 93%).

(B): [1-(4-Methoxy-naphthalene-1-sulfonyl)-1H-indole-3-yl]-piperazin-1-yl-methanone (6)

Prepared as in Example 1 (D). Positive ion ESI (M+H)$^+$ of 450.15.

Example 7

1-(4-Methoxy-naphthalene-1-sulfonyl)-1H-indole-3-carboxylic acid methyl-(1-methyl-piperidin-4-yl)-amide (7)

(A): 1-(4-Methoxy-naphthalene-1-sulfonyl)-1H-indole-3-carboxylic acid

Prepared as in Example 6 (A).

(B): 1-(4-Methoxy-naphthalene-1-sulfonyl)-1H-indole-3-carboxylic acid methyl-(1-methyl-piperidin-4-yl)-amide (7)

Prepared as in Example 1 (D). Positive ion ESI (M+H)$^+$ of 491.6.

Example 8

1-(4-Ethoxynaphthalene-1-sulfonyl)-2,3-dihydro-1H-indole-3-carboxylic acid homopiperazin-1-yl Amide (8)

(A): 1-Ethoxynaphthyl-4-sulfonyl Chloride

To a solution of 1-naphthol-4-sulfonic acid sodium salt (10 g, 40 mmol) in DMF (50 cm³) was added potassium carbonate (8.42 g, 60 mmol) and the resulting reaction mixture was allowed to stir for a few minutes. Ethyl iodide (3.6 cm³ 45 mmol) was added and the reaction was heated at 60° C. for 20 h. Upon cooling, it was diluted with methanol until 1-ethoxynaphthyl-4-sulfonic acid sodium salt precipitated as a white solid. This was collected by filtration (10 g, 39 mmol, 97%) before part of it (3.5 g, 14 mmol) was taken up in dichloromethane (20 cm³). This solution was cooled to 0° C. and phosphorus pentachloride (4.3 g, 20 mmol) was added portionwise. After stirring at room temperature for 2 h the reaction mixture was poured into dilute sodium bicarbonate solution and the product was extracted with dichloromethane (30 cm³). The organic layer was separated and concentrated under reduced pressure to provide the title compound as a solid (2.5 g, 9 mmol, 65%).

(B): 1-(4-Ethoxy-naphthalene-1-sulfonyl)-2,3-dihydro-1H-indole-3-carboxylic acid homopiperazin-1-yl Amide (8)

Prepared as in Example 1 (C-D). Positive ion ESI (M+H)$^+$ 480.2.

Example 9

2-[1-(4-Methoxy-naphthalene-1-sulfonyl)-2,3-dihydro-1H-indol-3-yl]-N-[3-(4-methyl-piperazin-1-yl)-propyl]-acetamide (9)

(A): Ethyl indole-3-acetate

Indole-3-acetic acid (3.5 g, 20 mmol) was dissolved in ethanol (70 Cm³) and a solution of hydrogen chloride in diethyl ether (12 cm³, 12 mmol) was added. The reaction was heated to reflux for 5 h and upon cooling the solvent was removed under reduced pressure to provide ethyl indole-3-acetate (4 g, 19 mmol, 98%) as a yellow oil.

(B): Ethyl-2,3-dihydro-indole-3-acetate

Ethyl indole-3-acetate (4 g, 19 mmol, 98%) was taken up in acetic acid (40 cm³) and sodium cyanoborohydride (4 g, 63 mmol) was added. The reaction was stirred at room temperature for 2 h, then diluted with aqueous sodium hydroxide until basic. The aqueous mixture was extracted with ethyl acetate and the organic layer was separated, dried and concentrated to dryness under reduced pressure. The solid obtained was taken up in dichloromethane and chromatographed on silica eluting with dichloro-methane with increasing volumes of methanol. The product containing fractions were combined and concentrated to yield ethyl-2,3-dihydro-indole-3-acetate as a solid (3 g, 15 mmol, 78%).

(C): Ethyl-1-(4-methoxynaphthylsulfonyl)-2,3-dihydroindole-3-acetic acid

4-Methoxynaphthylsulfonyl chloride (1.25 g, 5 mmol.) was added portionwise to ethyl-2,3-dihydro-1H indole-3-acetate (1 g, 5 mmol) in dichloromethane (20 cm³), containing triethylamine (1 cm³, 7 mmol) at 0° C. After stirring at room temperature for 4 h, the reaction was diluted with water and the organic layer was separated, dried and concentrated to give ethyl-1-(4-methoxynaphthylsulfonyl)-2,3-dihydroindole-3-acetate as an oil (2 g, 4.7 mmol, 94%). This was then taken up in ethyl alcohol (20 cm³) and aqueous sodium hydroxide (4N, 7 cm³, 28 mmol) was added and the resulting mixture was stirred and heated together at reflux for 2 h. The reaction mixture was then cooled and the ethyl alcohol was removed under reduced pressure. The residue was taken up in water and extracted once with diethyl ether to remove any unreacted ester. The aqueous mixture was then acidified and the product extracted into ethyl acetate. The organic layer was separated, dried and concentrated to provide 1-(4-methoxynaphthylsulfonyl)-2,3-dihydro-indole-3-acetic acid as a solid (1.17 g, 3.00 mmol, 64%).

(D): 2-[1-(4-Methoxynaphthalene-1-sulfonyl)-2,3-dihydro-1H-indol-3-yl]-N-[3-(4-methyl-piperazin-1-yl)-propyl]-acetamide (9)

Prepared as in Example 1 (D). Positive ion ESI (M+H)+ 537.3.

Using procedures similar to those described above (Examples 1-9) the following compounds were also prepared:

Example 10

1-(3,4-Dimethoxybenzenesulfonyl)-2,3-dihydro-1H-indole-3-carboxylic acid [3-(4-methyl-piperazin-1-yl)-propyl]-amide Prepared as in Example 1 (C-D). Positive ion ESI (M+H)+ 503.2.

Example 11

1-(4-Methoxy-2,3,6-trimethylbenzenesulfonyl)-2,3-dihydro-1H-indole-3-carboxylic acid methyl-(1-methyl-piperidin-4-yl)-amide Prepared as in Example 1 (C-D). Positive ion ESI (M+H)+ 486.2.

Example 12

1-(4-Methoxy-2,3,6-trimethylbenzenesulfonyl)-2,3-dihydro-1H-indole-3-carboxylic acid (1-methyl-piperidin-4-yl)-amide Prepared as in Example 1 (C-D). Positive ion ESI (M+H)+ of 586.6.

Example 13

1-(4-Methoxynaphthalene-1-sulfonyl)-2,3-dihydro-1H-indole-3-carboxylic acid [3-(2-methyl-piperidin-1-yl)-propyl]-amide Prepared as in Example 1 (D). Positive ion ESI (M+H)+ 522.5.

Example 14

1-(4-Methoxynaphthalene-1-sulfonyl)-2,3-dihydro-1H-indole-3-carboxylic acid (2-dimethylamino-1-methyl-ethyl)-amide Prepared as in Example 1 (D). Positive ion ESI (M+H)+ 468.5.

Example 15

[1-(4-Methoxynaphthalene-1-sulfonyl)-2,3-dihydro-1H-indol-3-yl](4-methyl-piperazin-1-yl)-methanone Prepared as in Example 1 (D). Positive ion ESI (M+H)+ 466.5.

Example 16

[1-(4-Methoxynaphthalene-1-sulfonyl)-2,3-dihydro-1H-indol-3-yl]-(4-methyl-[1,4]diazepan-1-yl)-methanone Prepared as in Example 1 (D). Positive ion ESI (M+H)+ 480.6.

Example 17

[1-(4-Methoxynaphthalene-1-sulfonyl)-2,3-dihydro-1H-indol-3-yl]-piperazin-1-yl-methanone Prepared as in Example 1 (D). Positive ion ESI (M+H)+ 452.6.

Example 18

[4]Diazepan-1-yl)-[1-(2,3,5,6-Tetramethylbenzenesulfonyl)-2,3-dihydro-1H-indol-3-yl]-methanone Prepared as in Example (C-D). Positive ion ESI (M+H)+ 442.5.

Example 19

1-(4-Methoxy-2,3-dimethylbenzenesulfonyl)-2,3-dihydro-1H-indole-3-carboxylic acid [2-(1-methyl-pyrrolidin-2-yl)-ethyl]-amide Prepared as in Example 4 (B-C). Positive ion ESI (M+H)+ 472.6.

Example 20

1-(4-Methoxy-2,3-dimethylbenzenesulfonyl)-2,3-dihydro-1H-indole-3-carboxylic acid [3-(2-methyl-piperidin-1-yl)-propyl]-amide Prepared as in Example 4 (B-C). Positive ion ESI (M+H)+ 500.6.

Example 21

1-(4-Methoxy-2,3-dimethylbenzenesulfonyl)-2,3-dihydro-1H-indole-3-carboxylic acid methyl-(1-methyl-piperidin-4-yl)-amide Prepared as in Example 4 (B-C). Positive ion ESI (M+H)+ 472.6.

Example 22

[1,4]Diazepan-1-yl)-[1-(4-Methoxy-2,3-dimethyl-benzenesulfonyl)-2,3-dihydro-1H-indol-3-yl]-methanone Prepared as in Example 4 (B-C). Positive ion ESI (M+H)+ 444.5.

Example 23

1-(4-Methoxy-2,3-dimethylbenzenesulfonyl)-2,3-dihydro-1H-indole-3-carboxylic acid (1-methyl-piperidin-4-yl)-amide Prepared as in Example 4 (B-C). Positive ion ESI (M+H)+ 458.5.

Example 24

1-(4-Methoxynaphthalene-1-sulfonyl)-2,3-dihydro-1H-indole-3-carboxylic acid (2-diethylamino-ethyl)-amide Prepared as in Example 1 (D). Positive ion ESI (M+H)+ 482.6.

Example 25

1-(4-Methoxynaphthalene-1-sulfonyl)-2,3-dihydro-1H-indole-3-carboxylic acid (1-methyl-piperidin-4-yl)-amide Prepared as in Example 1 (D). Positive ion ESI (M+H)+ 480.5.

Example 26

1-(4-Methoxynaphthalene-1-sulfonyl)-2,3-dihydro-1H-indole-3-carboxylic acid (3-imidazol-1-yl-propyl)-amide Prepared as in Example 1 (D). Positive ion ESI (M+H)+ 491.6.

Example 27

1-(4-Methoxynaphthalene-1-sulfonyl)-2,3-dihydro-1H-indole-3-carboxylic acid [4-methyl-piperidin-1-yl)-cyclohexyl]-amide Prepared as in Example 1 (D). Positive ion ESI (M+H)+ 562.7.

Example 28

1-(4-Methoxynaphthalene-1-sulfonyl)-2,3-dihydro-1H-indole-3-carboxylic acid [2-(2-piperidin-1-yl-ethyl)-piperidin-1-yl]amide Prepared as in Example 1 (D). Positive ion ESI (M+H)+ 562.7.

Example 29

1-(4-Methoxynaphthalene-1-sulfonyl)-2,3-dihydro-1H-indole-3-carboxylic acid (2-pyrrolidin-1-ylmethyl-pyrrolidin-1-yl)amide Prepared as in Example 1 (D). Positive ion ESI (M+H)+ 519.9.

Example 30

1-(4-Methoxynaphthalene-1-sulfonyl)-2,3-dihydro-1H-indole-3-carboxylic acid (3-diethylamino-propyl)-amide Prepared as in Example 1 (D). Positive ion ESI (M+H)+ 496.6.

Example 31

1-(4-Methoxynaphthalene-1-sulfonyl)-2,3-dihydro-1H-indole-3-carboxylic acid (8-methyl-8-aza-bicyclo[3.2.1]oct-3-yl)amide Prepared as in Example 1 (D). Positive ion ESI (M+H)+ 506.5.

Example 32

1-(4-Methoxynaphthalene-1-sulfonyl)-2,3-dihydro-1H-indole-3-carboxylic acid (4-methyl-piperazin-1-yl)-amide Prepared as in Example 1 (D). Positive ion ESI (M+H)+ 481.6.

Example 33

1-(4-Methoxynaphthalene-1-sulfonyl)-2,3-dihydro-1H-indole-3-carboxylic acid (1-benzyl-piperidin-4-yl)-amide Prepared as in Example 1 (D). Positive ion ESI (M+H)+ 556.8.

Example 34

[1,4]Diazepan-1-yl)-[1-(4-Methoxynaphthalene-1-sulfonyl)-2,3-dihydro-1H-indol-3-yl]-methanone Prepared as in Example 1 (D). Positive ion ESI (M+H)+ 550.7.

Example 35

1-(4-Methoxynaphthalene-1-sulfonyl)-2,3-dihydro-1H-indole-3-carboxylic acid methyl-(1-methyl-piperidin-4-yl)-amide Prepared as in Example 1 (D). Positive ion ESI (M+H)+ 494.6.

Example 36

1-[1,4]Diazepan-1-yl-2-[1-(4-methoxynaphthalene-1-sulfonyl)-2,3-dihydro-1H-indol-3-yl]-ethanone Prepared as in Example 9 (D). Positive ion ESI (M+H)+ of 480.2.

Example 37

2-[1-(4-Methoxynaphthalene-1-sulfonyl)-2,3-dihydro-1H-indol-3-yl]-1-piperazin-1-yl-ethanone Prepared as in Example 9 (D). Positive ion ESI (M+H)+ of 466.2.

Example 38

1-(Biphenyl-4-sulfonyl)-2,3-dihydro-1H-indole-3-carboxylic acid methyl-(1-methyl-piperidin-4-yl)-amide trifluoroacetate (38)

(A): 2,3-Dihydro-1H-indole-3-carboxylic acid

Prepared as in Example 1 (A).

(B): 2,3-Dihydro-1H-indole-3-carboxylic acid 1-tert-butyl ester

A suspension of 2,3-dihydro-1H-indole-3-carboxylic acid (A) (5 g, 30.6 mmol), di-tert-butyl dicarbonate (7.36 g, 33.7 mmol) and sodium bicarbonate (7.72 g, 91.9 mmol) in methanol (300 cm$^3$) was agitated in a sonic bath for 2 h at room temperature. The solution was evaporated to dryness under reduced pressure and the residue taken up in water (750 cm$^3$) and washed with dichloromethane (2×250 cm$^3$). The aqueous layer was then acidified to pH 4 with 2N hydrochloric acid and the organic material was extracted into ethyl acetate (500 cm$^3$). The organic layer was then washed with water (500 cm$^3$), dried over magnesium sulfate, filtered and the filtrate evaporated under reduced pressure to afford the title compound (B) (6.13 g, 23.3 mmol, 76%).

(C): 3-[Methyl-(1-methyl-piperidin-4-yl)-carbamoyl]-2,3-dihydro-indole-1-carboxylic acid tert-butyl ester To a solution of 2,3-dihydro-1H-indole-3-carboxylic acid 1-tert-butyl ester (B) (6.1 g, 23.3 mmol) in dichloromethane (200 cm$^3$) was added 1-hydroxybenzotriazole (HOBT, 8.28 g, 61.3 mmol) and 1-[3-(dimethylamino)propyl]-3-ethyl carbodiimide hydrochloride (EDC, 8.81 g, 45.9 mmol). This was left to stir at room temperature for 45 min, before addition of 1-methyl-4-(methylamino)piperidine (9.82 g, 76.5 mmol). The reaction was stirred for 16 h at room temperature. The solution was then washed with saturated aqueous sodium bicarbonate solution (200 cm$^3$), water (200 cm$^3$) and then saturated aqueous sodium chloride solution (200 cm$^3$) before the organic portion was dried over magnesium sulfate and filtered. The filtrate was then evaporated under reduced pressure to afford a brown residue, which was chromatographed on silica. Elution with dichloromethane→dichloromethane/methanol 95:5 gave the title compound (C) (3.93 g, 10.53 mmol, 45%).

(D): 2,3-Dihydro-1H-indole-3-carboxylic acid methyl-(1-methyl-piperidin-4-yl)-amide A solution of 3-[Methyl-(1-methyl-piperidin-4-yl)-carbamoyl]-2,3-dihydro-indole-1-carboxylic acid tert-butyl ester (C) (3.93 g, 10.53 mmol) in dichloromethane (20 cm$^3$) was cooled to 0° C. in an ice/water bath and trifluoroacetic acid (10 cm$^3$) added. The solution was stirred at 0° C. for 1 hr before warming to room temperature. The solution was made basic with saturated aqueous sodium bicarbonate solution and extracted with dichloromethane (3×100 cm$^3$). The organic layer was then dried over magnesium sulfate, filtered and evaporated under reduced pressure to afford the title compound (D) (2.79 g, 10.2 mmol, 97%).

(E): 1-(Biphenyl-4-sulfonyl)-2,3-dihydro-1H-indole-3-carboxylic acid methyl-(1-methyl-piperidin-4-yl)-amide Trifluoroacetate (38)

To a solution of biphenyl-4-sulfonyl chloride (2 mol. eq., 55 mg, 0.22 mmol) in N, N-dimethylformamide (DMF) (1 cm$^3$), was added 2,3-dihydro-1H-indole-3-carboxylic acid methyl-(1-methyl-piperidin-4-yl)-amide (D) (30 mg, 0.11 mmol) pre-dissolved in N, N-dimethylformamide (DMF) (0.5 cm$^3$), followed by N,N-diisopropylethylamine (0.1 cm$^3$, 0.57 mmol). The mixture was shaken at room temperature for 16 h before evaporation under reduced pressure. The residue was dissolved in N,N-dimethylformamide (DMF) (1 cm$^3$) and purified using reverse phase HPLC (Agilent Technologies, CombiHT SB-C18, Preparative cartridge 21.2×100 mm, 5-micron) using a linear gradient of water (0.1% trifluoroacetic acid)/acetonitrile (0.1% trifluoroacetic acid). The desired peak was then evaporated under reduced pressure to afford the title compound (38) (16.4 mg, 25%) positive ion APCI (M+H)+ 490.6.

Using procedures similar to those described above (Example 38) the following compounds were also prepared:

Example 39

1-(3-Trifluoromethyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)+ 482.5.

Example 40

1-(3-Bromo-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)+ 4934.

Example 41

1-(5-Chlorothiophene-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 455.0.

Example 42

1-(4-Trifluoromethoxy-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 498.5.

Example 43

1-(5-Bromo-thiophene-sulfonyl)-2,3-dihydro-1H-indole-3-carboxylic acid methyl-(1-methyl-piperidin-4-yl)-amide trifluoroacetate Prepared as in Example 38 (E) Positive ion APCI (M+H)$^+$ 499.4.

Example 44

1-(4-Bromo-5-chloro-thiophene-sulfonyl)-2,3-dihydro-1H-indole-3-carboxylic acid methyl-(1-methyl-(1-piperidin-4-yl)-amide trifluoroacetate Prepared as in Example 38 (E). Positive ion APCI (M+H)$^+$ 533.9.

Example 45

1-(Benzo[1,2,5]thiadiazole-4-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 472.5.

Example 46

1-(4-Methyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 428.5.

Example 47

1-(4,5-Dibromo-thiophene-sulfonyl)-2,3-dihydro-1H-indole-3-carboxylic acid methyl-(1-methyl-piperidin-4-yl)-amide trifluoroacetate Prepared as in Example 38 (E. Positive ion APCI (M+H)$^+$ 578.3.

Example 48

1-(Thiophene-2-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 420.5.

Example 49

1-(3,4-Dimethoxy-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 474.5.

Example 50

1-(4-Trifluoromethyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 482.5.

Example 51

1-(2,5-Dichloro-thiophene-3-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 489.4.

Example 52

1-(4-Acetyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 456.6.

Example 53

1-[4-(4-Fluoro-phenoxy)-benzenesulfonyl]-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 524.6.

Example 54

1-(3-Chloro-4-methyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 463.0.

Example 55

1-(2,3-Dihydro-benzofuran-5-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 456.5.

Example 56

1-(5-Isoixazol-3-yl-thiophene-2-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 487.6.

Example 57

1-(2,3-Dihydro-benzo[1,4]dioxine-6-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 472.5.

Example 58

1-(Naphthalene-2-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 464.5.

Example 59

1-(Naphthalene-1-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 464.5.

Example 60

1-(Biphenyl-3-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 490.6.

Example 61

1-(3-Phenoxy-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI M+H)$^+$ 506.6.

Example 62

1-(Benzo[b]thiophene-3-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 470.6.

Example 63

1-(5-Pyridin-2-yl-thiophene-2-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 497.6.

Example 64

1-(5-Chloro-3-methyl-benzo[b]thiophene-2-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 519.0.

Example 65

1-(6-Dimethylamino-naphthalene-1-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 507.6.

Example 66

3-{3-[Methyl-(1-methyl-piperidin-4-yl)-carbamoyl]-2,3-dihydro-indole-1-sulfonyl}-thiophene-2-carboxylic acid methyl ester trifluoroacetate Prepared as in Example 38 (E). Positive ion APCI (M+H)$^+$ 478.5.

Example 67

1-(4-Methoxy-3-methyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 458.5.

Example 68

1-(4-Methoxy-2,5-dimethyl-benzenesulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 472.6.

Example 69

1-(3-Bromo-4-methoxy-benzenesulfonyl)-2,3-dihydro-1H-indole-3-carboxylic acid methyl-(1-methyl-piperidin-4-yl)-amide trifluoroacetate Prepared as in Example 3 (E). Positive ion APCI (M+H)$^+$ 523.4.

Example 70

1-(3-Methylquinoline-8-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 479.6.

Example 71

1-(5-Chloro-naphthalene-1-sulfonyl)-2,3-dihydro-1H-indole-3-carboxylic acid methyl-(1-methyl-piperidin-4-yl)-amide trifluoroacetate Prepared as in Example 38 (E). Positive ion APCI (M+H)$^+$ 499.0.

Example 72

7-Bromo-1-(4-methoxy-naphthalene-1-sulfonyl)-1H-indole-3-carboxylic acid methyl-(1-methyl-piperidin-4-yl)-amide trifluoroacetate (72)

(A): 7-Bromo-1H-indole-3-carboxylic acid

To a solution of 7-bromoindole (10 g, 51.0 mmol) in N,N-dimethylformamide (DMF) (100 cm$^3$) was added trifluoroacetic anhydride (12.5 cm$^3$, 89.6 mmol) over 5 min. The resultant solution was stirred at room temperature for 16 h. The solution was poured onto water (500 cm$^3$) and the precipitate formed was isolated by filtration, washed with water and 4N sodium hydroxide (200 cm$^3$) added. The suspension was heated at reflux for 1.5 h and allowed to cool before washing with diethyl ether (2×250 cm$^3$). The aqueous layer was acidified to pH 1 with 5N hydrochloric acid and the resultant precipitate isolated by filtration, washed with water and dried over phosphorous pentoxide under reduced pressure at 60° C. for 16 h. This afforded the title compound LA) (8.94 g, 73%).

(B): 7-Bromo-1H-indole-3-carboxylic acid methyl-(1-methyl-piperidin-4-yl)-amide

To a solution of 7-Bromo-1H-indole-3-carboxylic acid (A) (240 mg, 1 mmol) in dichloromethane (8 cm$^3$) was added polystyrene-bound carbodiimide (1 g, loading 1.3 mmol/g, 1.3 mmol) followed by 1-methyl-4-(methylamino)piperidine (192 mg, 1.5 mmol) and the resulting suspension was gently shaken at room temperature for 16 h. The suspension was filtered and the resin washed with dichloromethane. The filtrate was then washed with saturated aqueous sodium bicarbonate solution, water before the organic portion was dried over magnesium sulfate, filtered and the filtrate evaporated under reduced pressure to give the title compound (B) (107.2 mg, 31%).

(C): 7-Bromo-1-(4-methoxy-naphthalene-1-sulfonyl)-1H-indole-3-carboxylic acid methyl-(1-methyl-piperidin-4-yl)-amide trifluoroacetate (72)

To a solution of 7-Bromo-1H-indole-3-carboxylic acid methyl-(1-methyl-piperidin-4-yl)-amide (B) (53.6 mg, 0.15 mmol) in dichloromethane (1.5 cm$^3$) and acetonitrile (0.5 cm$^3$) was added potassium fluoride on alumina (0.8 g, loading 1.3 mmol/g, 1.04 mmol) followed by a solution of 4-methoxy-naphthalene-1-sulfonyl chloride (128 mg, 0.5 mmol) in acetonitrile (1 cm$^3$) and the resulting suspension was gently shaken at room temperature for 16 h. The suspension was centrifuged for 5 min at 1000 rpm in order to isolate the filtrate. A further 5 cm$^3$ of dichloromethane was added and the suspension shaken for 10 min before being centrifuged again for 5 min at 1000 rpm. Again the filtrate was isolated and the organic portions combined and evaporated under reduced pressure. The residue was dissolved in N,N-dimethylformamide (DMF) (1 cm$^3$) and purified using reverse phase HPLC (Agilent Technologies, CombiHT SB-C18, Preparative cartridge 21.2×100 mm, 5-micron) using a linear gradient of water (0.1% trifluoroacetic acid)/acetonitrile (0.1% trifluoroacetic acid). The desired peak was then evaporated under reduced pressure to afford the title compound (72) (8.2 mg, 7.8%). Positive ion APCI (M+H)$^+$ 571.5.

Using procedures similar to those described above (Example 72) the following compounds were also prepared:

Example 73

5-Fluoro-1-(4-methoxy-naphthalene-1-sulfonyl)-1H-indole-3-carboxylic acid methyl-(1-methyl-piperidin-4-yl)-amide trifluoroacetate Prepared as in Example 72 (AC). Positive ion APCI (M+H)$^+$ 510.6.

Example 74

1-(4-Methoxy-naphthalene-1-sulfonyl)-5-methyl-1H-indole-3-carboxylic acid methyl-(1-methyl-piperidin-4-yl)-amide trifluoroacetate Prepared as in Example 72 (C). Positive ion APCI (M+H)$^+$ 506.7.

Example 75

5-Methoxy-1-(4-methoxy-naphthalene-1-sulfonyl)-1H-indole-3-carboxylic acid methyl-(1-methyl-piperidin-4-yl)-amide trifluoroacetate Prepared as in Example 72 (A-C). Positive ion APCI (M+H)$^+$ 522.7.

Example 76

2-[1-(4-Methoxy-naphthalene-1-sulfonyl)-2-methyl-1H-indol-3-yl]-N-methyl-N-(1-methyl-piperidin-4-yl)-acetamide trifluoroacetate Prepared as in Example 72 (A-C). Positive ion APCI (M+H)$^+$ 520.7.

Example 77

1-(5-Bromo-thiophene-2-sulfonyl)-7-ethyl-1H-indole-3-carboxylic acid methyl-(1-methyl-piperidin-4-yl)-amide trifluoroacetate Prepared as in Example 72 (A-C). Positive ion APCI (M+H)$^+$ 525.5.

Example 78

1-(5-Bromo-thiophene-2-sulfonyl)-5-fluoro-1H-indole-3-carboxylic acid methyl-(1-methyl-piperidin 4-yl)-amide trifluoroacetate Prepared as in Example 72 (A-C). Positive ion APCI (M+H)$^+$ 515.5.

Example 79

1-(5-Bromo-thiophene-2-sulfonyl)-5-methoxy-1H-indole-3-carboxylic acid methyl-(1-methyl-piperidin-4-yl)-amide trifluoroacetate Prepared as in Example 72 (A-C). Positive ion APCI (M+H)$^+$ 527.5.

Example 80

1-(5-Bromo-thiophene-2-sulfonyl)-2-methyl-1H-indole-3-carboxylic acid methyl-(1-methyl-piperidin-4-yl)-amide trifluoroacetate Prepared as in Example 72 (A-C). Positive ion APCI (M+H)$^+$ 511.5.

Example 81

2-[1-(5-Bromo-thiophene-2-sulfonyl)-2-methyl-1H-indol-3-yl]-N-methyl-N-(1-methyl-piperidin-4-yl)-acetamide trifluoroacetate Prepared as in Example 72 (C). Positive ion APCI (M+H)$^+$ 525.5.

Example 82

2-[1-(5-Bromo-thiophene-2-sulfonyl)-5-methoxy-1H-indol-3-yl]-N-methyl-N-(1-methyl-piperidin-4-yl)-acetamide trifluoroacetate Prepared as in Example 72 (A-C). Positive ion APCI (M+H)$^+$ 541.5.

Example 83

[5-Bromo-1-(4-methoxy-naphthalene-1-sulfonyl)-1H-indol-3-yl]-[1,4]diazepan-1-yl-methanone trifluoroacetate (83)

(A): 4-[5-Bromo-1-(4-methoxy-naphthalene-1-sulfonyl)-1H-indole-3-carbonyl]-[1,4]diazepane-1-carboxylic acid tert-butyl ester Prepared as in Example 72 (A-C).

(B): [5-Bromo-1-(4-methoxy-naphthalene-1-sulfonyl)-1H-indol-3-yl]-[1,4]diazepan-1-yl-methanone trifluoroacetate (83)

To a solution of 4-[5-Bromo-1-(4-methoxy-naphthalene-1-sulfonyl)-1H-indole-3-carbonyl]-[1,4]diazepane-1-carboxylic acid tert-butyl ester (A) (45 mg, 0.07 mmol) in dichloromethane (5 cm$^3$) was added trifluoroacetic acid (2 cm$^3$). The solution was shaken at room temperature for 1 h before the solvent was removed under reduced pressure. The residue was dissolved in N,N-dimethylformamide (DMF) (1 cm$^3$) and purified using reverse phase HPLC (Agilent Technologies, CombiHT SB-C18, Preparative cartridge 21.2×100 mm, 5-micron) using a linear gradient of water (0.1% trifluoroacetic acid)/acetonitrile (0.1% trifluoroacetic acid). The desired peak was then evaporated under reduced pressure to afford the title compound (83) (45.9 mg, 27%). Positive ion APCI (M+H)$^+$ 543.4.

Using procedures similar to those described above (Examples 72 and 83) the following compounds were also prepared:

Example 84

[1,4]Diazepan-1-yl-[5-fluoro-1-(4-methoxy-naphthalene-1-sulfonyl)-1H-indol-3-yl]-methanone trifluoroacetate (84)

(A): 4-[5-Fluoro-1-(4-methoxy-naphthalene-1-sulfonyl)-1H-indole-3 carbonyl]-[1,4]diazepane-1-carboxylic acid tert-butyl ester Prepared as in Example 72 (A-C).

(B): [1,4]Diazepan-1-yl-[5-fluoro-1-(4-methoxy-naphthalene-1-sulfonyl)-1H-indol-3-yl]-methanone trifluoroacetate (84)

Prepared as in Example 83 (A-B). Positive ion APCI (M+H)$^+$ 482.5.

Example 85

[1,4]Diazepan-1-yl-[1-(4-methoxy-naphthalene-1-sulfonyl)-5-methyl-1H-indol-3-yl]-methanone trifluoroacetate (85)

(A): 4-[1-(4-Methoxy-naphthalene-1-sulfonyl)-5-methyl-1H-indole-3-carbonyl]-[1,4]-diazepane-1-carboxylic acid tert-butyl ester Prepared as in Example 72 (A-C).

(B): [1,4]Diazepan-1-yl-[1-(4-methoxy-naphthalene-1-sulfonyl)-5-methyl-1H-indol-3-yl]-methanone trifluoroacetate (85)

Prepared as in Example 83 (A-B). Positive ion APCI (M+H)$^+$ 478.5.

Example 86

[1,4]Diazepan-1-yl-[5-methoxy-1-(4-methoxy-naphthalene-1-sulfonyl)-1H-indol-3-yl]-methanone trifluoroacetate (86)

(A): 4-[5-Methoxy-1-(4-methoxy-naphthalene-1-sulfonyl)-1H-indole-3-carbonyl]-[1,4]diazepane-1-carboxylic acid tert-butyl ester Prepared as in Example 72 (A-C).

(B): [1,4]Diazepan-1-yl-[5-methoxy-1-(4-methoxy-naphthalene-1-sulfonyl)-1H-indol-3-yl]-methanone trifluoroacetate (86)

Prepared as in Example 83 (A-B). Positive ion APCI (M+H)$^+$ 494.5.

Example 87

[1,4]Diazepan-1-yl-[1-(4-methoxy-naphthalene-1-sulfonyl)-2-methyl-1H-indol-3-yl]-methanone trifluoroacetate (87)

(A): 4-[1-(4-Methoxy-naphthalene-1-sulfonyl)-2-methyl-1H-indole-3-carbonyl]-[1,4]diazepane-1-carboxylic acid tert-butyl ester Prepared as in Example 72 (A-C).

(B): [1,4]Diazepan-1-yl-[1-(4-methoxy-naphthalene-1-sulfonyl)-2-methyl-1H-indol-3-yl]methanone trifluoroacetate (87)

Prepared as in Example 83 (A-B). Positive ion APCI (M+H)$^+$ 478.5.

Example 88

1-[1,4]Diazepan-1-yl-2-[1-(4-methoxy-naphthalene-1-sulfonyl)-2-methyl-1H-indol-3-yl]-ethanone trifluoroacetate (88)

(A): 4-{2-[1-(4-Methoxy-naphthalene-1-sulfonyl)-2-methyl-1H-indol-3-yl]-acetyl}-[1,4]diazepane-1-carboxylic acid tert-butyl ester Prepared as in Example 72 (A-C).

(B): 1-[1,4]Diazepan-1-yl-2-[1-(4-methoxy-naphthalene-1-sulfonyl)-2-methyl-1H-indol-3-yl]-ethanone trifluoroacetate (88)

Prepared as in Example 83 (A-B). Positive ion APCI (M+H)$^+$ 492.6.

Example 89

1-[1,4]Diazepan-1-yl-2-[5-methoxy-1-(4-methoxy-naphthalene-1-sulfonyl)-1H-indol-3-yl]-ethanone trifluoroacetate (89)

(A): 4-{2-[5-Methoxy-1-(4-methoxy-naphthalene-1-sulfonyl)-1H-indol-3-yl]-acetyl}-[1,4]diazepane-1-carboxylic acid tert-butyl ester Prepared as in Example 72 (A-C).

(B): 1-[1,4]Diazepan-1-yl-2-[5-methoxy-1-(4-methoxy-naphthalene-1-sulfonyl)-1H-indol-3-yl]-ethanone trifluoroacetate (89)

Prepared as in Example 83 (A-B). Positive ion APCI (M+H)$^+$ 508.6.

Example 90

[7-Bromo-1-(5-bromo-thiophene-2-sulfonyl)-1H-indol-3-yl]-[1,4]diazepan-1-yl-methanone trifluoroacetate (90)

(A): 4-[7-Bromo-1-(5-bromo-thiophene-2-sulfonyl)-1H-indol-3-carbonyl]-[1,4]diazepane-1-carboxylic acid tert-butyl ester Prepared as in Example 72 (A-C).

(B): [7-Bromo-1-(5-bromo-thiophene-2-sulfonyl)-1H-indol-3-yl]-[1,4]diazepan-1-yl-methanone trifluoroacetate (90)

Prepared as in Example 83 (A-B). Positive ion APCI (M+H)$^+$ 548.3.

Example 91

1-(4-Methoxynaphthalene-1-sulfonyl)-2,3-dihydro-1H-indole-3-carboxylic acid (2-morpholin-4-yl-ethyl)-amide trifluoroacetate (91)

(A): 1-(4-methoxynaphthalene-1-sulfonyl)-2,3-dihydro-1H-indole-3-carboxylic acid Prepared as in Example 1 (A-C).

(B): 1-(4-Methoxynaphthalene-1-sulfonyl)-2,3-dihydro-1H-indole-3-carboxylic acid (2-morpholin-4-yl-ethyl)-amide trifluoroacetate (91)

To a solution of 1-(4-methoxynaphthalene-1-sulfonyl)-2,3-dihydro-1H-indole-3-carboxylic acid (A) (10 mg, 0.026 mmol) in dichloromethane (1 cm$^3$) was added 2-morpholin-4-yl-ethylamine (3.4 mg, 0.026 mmol) as a 1% solution in dichloromethane and polystyrene-bound carbodiimide (50 mg, loading 1.3 mmol/g, 0.065 mmol). The resulting mixture was gently stirred at 20° C. for 18 h, filtered and the filtrate evaporated under reduced pressure. The residue was purified using reverse phase HPLC (Agilent Technologies, CombiHT SB-C18, preparative cartridge 21.2×100 mm, 5-micron) using a linear gradient of water (0.1% trifluoroacetic acid)/acetonitrile (0.1% trifluoroacetic acid). The desired peak was then evaporated under reduced pressure to afford the title compound (91) (2.3 mg, 18%) Positive ion ESI (M+H)$^+$ 496.0.

Using procedures similar to that described above (Example 91) the following amides were prepared from commercially available amines:

Example 92

1-(4-Methoxy-naphthalene-1-sulfonyl)-2,3-dihydro-1H-indole-3-carboxylic acid benzyl-(2-dimethylamino-ethyl)-amide trifluoroacetate Prepared as in Example 91 (B). Positive ion ESI (M+H)$^+$ 544.0.

Example 93

[4-(2-Dimethylamino-ethyl)-piperazin-1-yl]-[1-(4-methoxy-naphthalene-1-sulfonyl)-2,3-dihydro-1H-indole-3-yl]-methanone trifluoroacetate Prepared as in Example 91 (B). Positive ion ESI (M+H)$^+$ 523.2.

Example 94

[1-(4-Methoxy-naphthalene-1-sulfonyl)-2,3-dihydro-1H-indol-3-yl]-(4-phenyl-piperazin-1-yl)-methanone trifluoroacetate Prepared as in Example 91 (B). Positive ion ESI (M+H)$^+$ 528.0.

Example 95

[1-(4-Methoxy-naphthalene-1-sulfonyl)-2,3-dihydro-1H-indol-3-yl]-(2,3,5,6-tetrahydro-[1,2']bipyrazinyl-4-yl)-methanone trifluoroacetate Prepared as in Example 91 (B). Positive ion ESI (M+H)$^+$ 530.0.

Example 96

(Hexahydro-pyrrolo[1.2-a]pyrazin-2-yl)-[1-(4-methoxynaphthalene-1-sulfonyl)-2,3-dihydro-1H-indol-3-yl]-methanone trifluoroacetate Prepared as in Example 91 (B). Positive ion ESI (M+H)$^+$ 492.1.

Example 97

1-(4-Methoxy-naphthalene-1-sulfonyl)-2,3-dihydro-1H-indole-3-carboxylic acid (3-morpholin-4-yl-propyl)-amide trifluoroacetate Prepared as in Example 91 (B) Positive ion ESI (M+H)$^+$ 510.4.

Example 98

1-(4-methoxy-naphthalene-1-sulfonyl)-2,3-dihydro-1H-indol-3-carboxylic acid methyl-(2-pyridin-4-yl-ethyl)-amide trifluoroacetate Prepared as in Example 91 (B). Positive ion ESI (M+H)$^+$ 502.0.

Example 99

1-(4-Methoxy-naphthalene-1-sulfonyl) 2,3-dihydro-1H-indole-3-carboxylic acid methyl-(2-pyridin-2-yl-ethyl)-amide trifluoroacetate Prepared as in Example 91 (B). Positive ion ESI (M+H)$^+$ 502.0.

Example 100

[1-(4-Methoxy-naphthalene-1-sulfonyl)-2,3-dihydro-1H-indol-3-yl]-[4-(3-methoxy-phenyl)-piperazin-1-yl]-methanone trifluoroacetate Prepared as in Example 91 (B). Positive ion ESI (M+H)$^+$ 558.2.

Further examples were prepared by the same method (Example 91) using amines prepared by previously published procedures. (J. Med. Chem. 44, 2679-2682.)

Example 101

1-(4-Methoxy-naphthalene-1-sulphonyl)-2,3-dihydro-1H-indole-3-carboxylic acid [2-dimethylamino-2-(4-methoxy-phenyl)-ethyl]-amide trifluoroacetate Prepared as in Example 91 (B). Positive ion ESI (M+H)$^+$ 560.2.

Example 102

1-(4-Methoxy-naphthalene-1-sulfonyl)-2,3-dihydro-1H-indole-3-carboxylic acid (2-dimethylamino-2-phenyl-propyl)-amide trifluoroacetate Prepared as in Example 91 (B). Positive ion ESI (M+H)$^+$ 544.2.

Example 103

1-(4-Methoxy-naphthalene-1-sulfonyl)-2,3-dihydro-1H-indole-3-carboxylic acid (1-dimethylamino-cyclohexylmethyl)-amide trifluoroacetate Prepared as in Example 91 (S. Positive ion ESI (M+H)$^+$ 522.3.

Example 104

1-(4-Methoxy-naphthalene-1-sulfonyl)-2,3-dihydro-1H-indole-3-carboxylic acid (1-dimethylamino-cyclopentylmethyl)-amide trifluoroacetate Prepared as in Example 91 (B). Positive ion ESI (M+H)$^+$ 508.3.

Example 105

(3-Amino-azetidin-1-yl)-[1-(4-methoxy-naphthalene-1-sulfonyl)-2,3-dihydro-1H-indol-3-yl]-methanone trifluoroacetate (105)

(A): 1-(4-methoxynaphthalene-1-sulfonyl)-2,3-dihydro-1H-indole-3-carboxylic acid Prepared as in Example 1 (A-C).

(B): (3-Amino-azetidin-1-yl)-[1-(4-methoxy-naphthalene-1-sulfonyl)-2,3-dihydro-1H-indol-3-yl]-methanone trifluoroacetate (105)

To a solution of 1-(4-methoxynaphthalene-1-sulfonyl)-2,3-dihydro-1H-indole-3-carboxylic acid (A) (10 mg, 0.026 mmol) in dichloromethane (1 cm$^3$) was added azetidine-3-yl-carbamic acid-t-butyl ester (4.5 mg, 0.026 mmol) as a 1% solution in dichloromethane and polystyrene-bound carbodimide (50 mg, loading 1.3 mmol/g, 0.065 mmol). The resulting mixture was gently stirred at 20° C. for 18 h, then filtered, and evaporated under reduced pressure to half volume. Trifluoroacetic acid (0.15 cm$^3$) was added and the solution was allowed to stand for one hour, then evaporated under reduced pressure. The residue was purified using reverse phase HPLC (Agilent Technologies, CombiHT SB-C18, preparative cartridge 21.2×100 mm, 5-micron) using a linear gradient of water (0.1% trifluoroacetic acid)/acetonitrile (0.1% trifluoroacetic acid). The desired peak was then evaporated under reduced pressure to afford the title compound (105) Positive ion ESI (M+H)$^+$ 438.1.

Using procedures similar to that described above (Example 105) the following compound was also prepared:

Example 106

(3-Aminomethyl-azetidine-1-yl)-[1-(4-methoxy-naphthalene-1-sulfonyl)-2,3-dihydro-1H-indol-3-yl]-methanone trifluoroacetate Prepared as in Example 105 (B). Positive ion ESI (M+H)$^+$ 452.0.

Example 107

1-(4-(Pyridin-4-yloxy)-benzene)-2,3-dihydro-1H-indole-3-carboxylic acid methyl-(1-methyl-piperidin-4-yl)-amide (A): 2,3-Dihydro-1H-indole-3-carboxylic acid methyl-(1-methyl-piperidin-4-yl)-amide Prepared as in Example 38 (A-D).

(B): 1-[4-(Pyridin-4-yloxy)-benzenesulphonyl]-2,3-dihydro-1H-indole-3-carboxylic acid methyl-(1-methyl-piperidyn-4-yl)-amide To a solution of 2,3-Dihydro-1H-indole-3-carboxylic acid methyl-(1-methyl-piperidin-4-yl)-amide (A) (20 mg, 0.07 mmol) in dichloromethane (1.0 cm$^3$) was added 4-(Pyridin-4-yloxy)-benzenesulphonyl chloride (29.1 mg, 0.095 mmol) and PS-Di-isopropylethylamine (60 mg, 0.22 mmol). The reaction was agitated overnight. PS-Trisamine (20 mg, 0.08 mmol) was added and the reaction agitated for 2 h. Filtration afforded the title compound (107) as a solid (26.9 mg, 98%) Positive ion ESI (M+H)$^+$ 507.1.

Example 108

1-(4-Phenyl-5-trifluoromethyl-thiophene-3-sulphonyl)-2,3-dihydro-1H-indole-3-carboxylic acid methyl-(1-methyl-piperidin-4-yl)-amide Prepared as in Example 107 (B). Positive ion ESI (M+H)$^+$ 564.2.

Example 109

1-(5-Methyl-2-trifluoromethyl-furan-3-sulphonyl)-2,3-dihydro-1H-indole-3-carboxylic acid methyl-(1-methyl-piperidin-4-yl)-amide Prepared as in Example 107 (B). Positive ion ESI (M+H)$^+$ 486.1.

Example 110

5-HT$_6$ Receptor Binding Assay

NIH 3T3 cells stably expressing the human 5-HT$_6$ gene were grown at 37° C. in a 5% CO$_2$ atmosphere in DMEM supplemented with 10% cosmic calf serum (Hyclone) and subcultured when confluent. Cells were harvested by trypsination (Sigma) and membranes prepared by homogenisation followed by centrifugation in 50 nmol·L$^{-1}$ Tris buffer (pH 7.4) containing 10 nmol·L$^{-1}$ magnesium sulphate and 0.5 nmol·L$^{-1}$ EDTA. Radioligand binding assays were performed in 96 well polystyrene deep well plates (Semat) in a final volume of 500 µl, consisting of 100 µl of competing drug, 100 µl of 10 nmole·L$^{-1}$ [$^3$H]-lysergic acid diethylamide (LSD) and 300 µl of diluted membrane expressing the 5-HT6 receptor. All test compounds were dissolved in DMSO (dimethyl-sulfoxide) at 10 mM and serially diluted is assay buffer to give a six-fold concentration range (between 0.01 nM and 100 µM). Non-specific binding was determined with 10 µM Methiothepin. Plates were incubated at room temperature for 90 minutes. The reactions were terminated by rapid filtration using a Packard harvester onto 96 well GF/B filter plates (Packerd Unifilter) presoaked with 0.3% w/N polyethylene-imine, washed 3 times with ice-cold assay buffer (1 ml), oven dried and 50 µl Microscint-20 added. The retained radioactivity was then determined using a scintillation counter.

Data were analysed using standard curve fitting procedures (Graphpad: four parameter logistic equation) to produce IC$_{50}$ values for active compounds (where IC$_{50}$ is the concentration of test compound causing 50% inhibition of binding). IC$_{50}$ values were conerted to pKi values using the Cheng-Prusoff equation 1 (Cheng, Y. and Prosoff, W. H., Biochem. Pharmacol. 22, 3099-3108, 1973).

The disclosed compounds of the invention have a selective affinity for the 5-HT$_6$ receptor characterized by a pKi value higher than 6.5.

Preferred compounds (those described in Examples 1, 2, 8, 17, 24, 25, 31, 34, 35, 39, 40, 42, 43, 44, 47, 50, 51, 55, 58, 59, 60, 62, 69, 71 and 109 have an affinity with a pKi higher than 7.5.

The invention claimed is:
1. A 1-arylsulfonyl-3-substituted indole or indoline compound having the general formula I

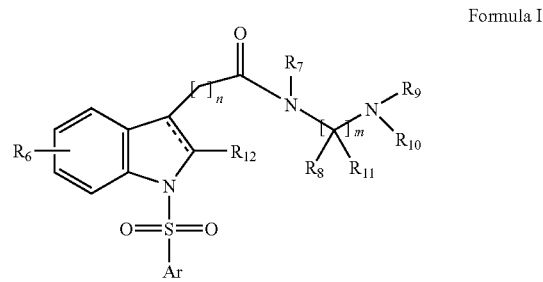

Formula I wherein
Ar is selected from phenyl, biphenyl, naphthyl, thienyl, furyl, benzothienyl, benzothiadiazolyl, 2,3-dihydrobenzofuranyl, 2,3-dihydrobenzodioxinyl, quinolinyl, and isoquinolinyl, Ar being optionally substituted with 1-5 substitutents selected from halogen, (C$_{1-4}$)alkyl (optionally substituted with halogen), (C$_{1-4}$)alkyloxy (optionally substituted with halogen), (C$_{6-12}$)aryl (optionally substituted with halogen or (C$_{1-4}$)alkyloxy), (C$_{6-12}$)aryloxy (optionally substituted with halogen), di($C_{1-4}$)alkylamino, ($C_{1-4}$)alkanoyl or ($C_{1-4}$)alkanoylamino;

the dotted line represents an optional bond;

n is 0 or 1;

m is 2-3;

$R_6$ represents 1-4 substituents independently selected from H, ($C_{1-4}$)alkyl (optionally substituted with halogen), ($C_{1-4}$)alkyloxy (optionally substituted with halogen), ($C_{1-4}$)alkyloxycarbonyl, cyano, nitro and halogen;

$R_7$ together with $R_9$ complete a 7-membered saturated ring;

each $R_8$ is independently H, ($C_{1-4}$) alkyl or ($C_{6-12}$)aryl (optionally substituted with halogen, ($C_{1-4}$)alkyl or ($C_{1-4}$)alkyloxy);

and $R_{10}$ is H, ($C_{1-4}$)alkyl, ($C_{6-12}$)aryl or ($C_{6-12}$)aryl($C_{1-4}$)alkyl;

each $R^{11}$ is independently H or ($C_{1-4}$)alkyl; or a pharmaceutically acceptable salt thereof.

2. The 1-arylsulfonyl-3-substituted indole or indoline compound of claim 1, wherein the Ar is selected from phenyl, naphthyl, thienyl and benzothienyl.

3. The 1-arylsulfonyl-3-substituted indole or indoline derivative of claim 1, wherein m is 2, all of $R_8$ and $R_{11}$ are H, $R_{10}$ is H or ($C_{1-4}$)alkyl.

4. The 1-arylsulfonyl-3-substituted indole or indoline compound of claim 1, wherein n is 0.

5. A pharmaceutical composition, comprising:

the 1-arylsulfonyl-3-substituted indole or indoline compound of formula I or a pharmaceutically acceptable salt thereof, as according to claim 1 and a pharmaceutically acceptable carrier therefore.

6. A method of treating a disorder selected from psychosis, schizophrenia, manic depressions, depressions, neurological disorders, cognitive enhancement, Parkinson's disease, amyotrophic lateral sclerosis, Alzheimer's disease or Huntington's disease, in a patient in need thereof comprising administering to the patient an effective amount of a 1-arylsulfonyl-3-substituted indole or indoline compound of claim 1.

* * * * *